United States Patent [19]

Carle et al.

[11] Patent Number: 4,737,251
[45] Date of Patent: Apr. 12, 1988

[54] FIELD-INVERSION GEL ELECTROPHORESIS

[75] Inventors: Georges F. Carle; Maynard V. Olson, both of St. Louis, Mo.

[73] Assignee: Washington University, St. Louis, Mo.

[21] Appl. No.: 781,283

[22] Filed: Sep. 27, 1985

[51] Int. Cl.[4] ........................................... G01N 27/26
[52] U.S. Cl. .............................. 204/182.8; 204/299 R
[58] Field of Search ......................... 204/182.8, 299 R

[56] References Cited

U.S. PATENT DOCUMENTS 3,506,554 4/1970 Broome ........................... 204/299 R
3,870,612 3/1975 Flygare et al. ............... 204/182.8 X
4,312,727 1/1982 Shainoff ........................... 204/182.8

FOREIGN PATENT DOCUMENTS 1046370 12/1958 Fed. Rep. of Germany .

Primary Examiner—John F. Niebling
Assistant Examiner—John S. Starsiak, Jr.
Attorney, Agent, or Firm—Ciotti & Murashige, Irell & Manella

[57] ABSTRACT

Disclosed herein is a method and apparatus for gel electrophoresis which employs periodic inversion of the electric field essentially in one dimension. According to this system, which is defined herein as field-inversion gel electrophoresis, net migration is achieved by using a longer time or higher voltage in one direction than in the other direction.

20 Claims, 2 Drawing Sheets

FIELD-INVERSION GEL ELECTROPHORESIS

BACKGROUND OF THE INVENTION

This invention relates to gel electrophoresis and more particularly to a method and apparatus for gel electrophoresis which employs periodic inversion of the electric field.

Electrophoresis involves the separation of mixtures by differential migration of components through a transport medium in an electric field. Many particles in aqueous solution acquire an electrical charge due to ionization and thus move in response to an external electric field. The charged particles may be simple ions, complex macromolecules, viruses, colloids or even living cells. The rate of their migration depends upon the amount of charge, the size and shape of the particle, and the properties of the solvent.

Electrophoresis in a gel medium is an important method of separating proteins, nucleic acids and other such macromolecules in mixture. When an electric field is applied to the medium at a given pH, the macromolecules migrate toward the oppositely charged electrode. The higher their ratio of charge to mass, the faster they move. The mixture of macromolecules is thereby eventually separated into a series of distinct bands in order of charge density. The electrophoresis is generally terminated when the leading band has migrated through most of the available gel. The bands can be identified by suitable means such as staining, optical scanning and the like procedures, and the macromolecules can be recovered by cutting out and solubilizing the corresponding portions of the gel. This can be done, for example, by electroelution from the gel or by chemical or physical disruption of the gel structure followed by appropriate purification techniques.

Agarose, which is a naturally occurring linear polysaccharide of galactose and 3,6-anhydrogalactose, is particularly useful as the electrophoretic support medium since it permits the separation of very large molecules such as viruses, enzyme complexes, lipoproteins and nucleic acids which are often outside the useful pore size with polyacylamide gel electrophoresis. A large variety of agaroses and modified agaroses are available commercially. They are usually used in concentrations ranging from about 0.1 to about 2.5% by weight.

Notwithstanding the foregoing, the use of conventional agarose gel electrophoresis has not generally been ideally suited for separation of the largest deoxyribonucleic acid (DNA) molecules, that is, molecules which are larger than about $2 \times 10^5$ base pairs (bp). Most practical work has been confined to molecules less than about $2 \times 10^4$ bp. Although typical DNA molecules employed in genetic engineering applications are within this lower size range, the DNA molecules in chromosomes are larger.

Further background information on conventional gel electrophoresis of DNA can be had by reference to a text such as Rickwood and Hames, *Gel Electrophoresis of Nucleic Acids: A Practical Approach*, IRL Press, Oxford, UK, particularly Chapter 2, "Gel Electrophoresis of DNA", by Sealey and Southern.

For background information on attempts to achieve separation of very large DNA molecules by conventional gel electrophoresis, reference can be had to papers by Fangman, *Nucleic Acids Res.* 5, 653-665 (1978); and Serwer, *Biochemistry* 19, 3001-3004 (1980). In the former paper, using very dilute agarose gels (which are difficult to handle) and low voltages (which require long running times), Fangman was able to achieve a mobility ratio of bacteriophage G DNA (approximately 750 kb, where 1 kb = 1 kilobase pair = 1000 base pairs) to bacteriophage T4 DNA (approximately 170 bp) of approximately 1.4. Molecules larger than bacteriophage G were not investigated. So also in the latter paper, Serwer found that the best conditions involved dilute agarose gels run at low voltages. Molecules larger than approximately 170 kb were not investigated.

Recently, a modified gel electrophoresis technique for separating large DNA molecule was disclosed by Schwartz et al., *Cold Spring Harbor Symp. Quant. Biol.* 47, 189-195 (1983); Schwartz and Cantor, *Cell* 37, 67-75 (1984); and Cantor and Schwartz, U.S. Pat. No. 4,473,452. According to their disclosed technique, the DNA molecules are separated by subjecting the gel medium to two non-uniform electric fields having coplanar directions which are transverse to each other. The DNA molecules thereby migrate in a direction that lies in between the two field directions. Although the disclosed Cantor and Schwartz technique has been applied with success to separate DNA molecules present in the chromosomes of lower organisms such as yeast and protozoans, the bands are somewhat distorted and nonparallel, whereby it is difficult to make lane-to-lane comparisons between samples as is obtained in conventional gel electrophoresis. Moreover, the transverse-field gel electrophoresis technique requires complex electrode geometries. Although the theoretical minimum is three, no devices have been described that contain fewer than four, and it is common for devices to feature whole arrays of electrodes. Furthermore, the precise positioning of the electrodes has dramatic effects on the results obtained. Consequently, transverse-field-alternation gel electrophoresis does not provide for convenient gel electrophoretic practice.

Implementation of the transverse-field technique (also defined as orthogonal-field-alternation) and applications to the chromosomal DNA molecules from yeast are described by Carle and Olson, *Nucleic Acids Res.* 12, 5647-5664 (1984). A description of the complete analysis of the set of chromosomal DNA molecules from yeast using the transverse-field technique is further reported by Carle and Olson, *Proc. Natl. Acad. Sci. U.S.A.* 82, 3756-3760 (1985).

Other background information on the application of the transverse-field technique of gel electrophoresis to chromosomal DNA molecules is provided by Van der Ploeg et al., *Cell* 37, 77-84 (1984); Van der Ploeg et al., *Cell* 39, 213-221 (1984); and Van der Ploeg et al., *Science* 229, 658-661 (1985).

BRIEF DESCRIPTION OF THE INVENTION

In accordance with the present invention, an improved system for gel electrophoresis has been devised which is suitable for the separation of very large DNA molecules, such as chromosomal DNA, and which provides parallel bands of the separated components. The method and apparatus of this invention employs periodic inversion of an electric field essentially in one dimension. In essence, this system can be described as field-inversion gel electrophoresis.

According to the invention, net migration is achieved by using a longer time or a higher voltage in one direction than in the other direction. Thus, net migration in a given direction can be achieved, for example, by partitioning each switching cycle unequally between so-called "forward" and "reverse" directions or by imposing a higher voltage in the forward direction than in the reverse direction, and vice versa. Resolution can be optimized in a given size range by selecting an appropriate switching regime. Conversely, a broad size range can be explored at lower resolution by employing temporal switching-interval gradients, in which the period or internal structure of the switching cycle is varied during an electrophoresis run.

The successful results achieved with the field-inversion gel electrophoresis system of this invention were surprising and unexpected in view of prior experience with electrophoresis. They were also not predictable from existing molecular theories of electrophoresis. Although the inventors are not bound by theory, the phenomenology of the system is believed to be based on the adoption of directional conformations by macromolecules during the electrophoresis as will be seen from specific examples and explanation hereinafter.

For many types of macromolecular mixtures, the present invention provides substantial improvements over the transverse-field technique in resolution, experimental convenience, and practical-sample capacity.

BRIEF DESCRIPTION OF THE DRAWINGS

While the specification concludes with claims particularly pointing out and distinctly claiming the subject matter regarded as forming the present invention, it is believed that the invention will be better understood from the following detailed description of preferred embodiments of the invention taken in connection with the accompanying drawings in which:

DETAILED DESCRIPTION OF THE INVENTION

Figure 1:
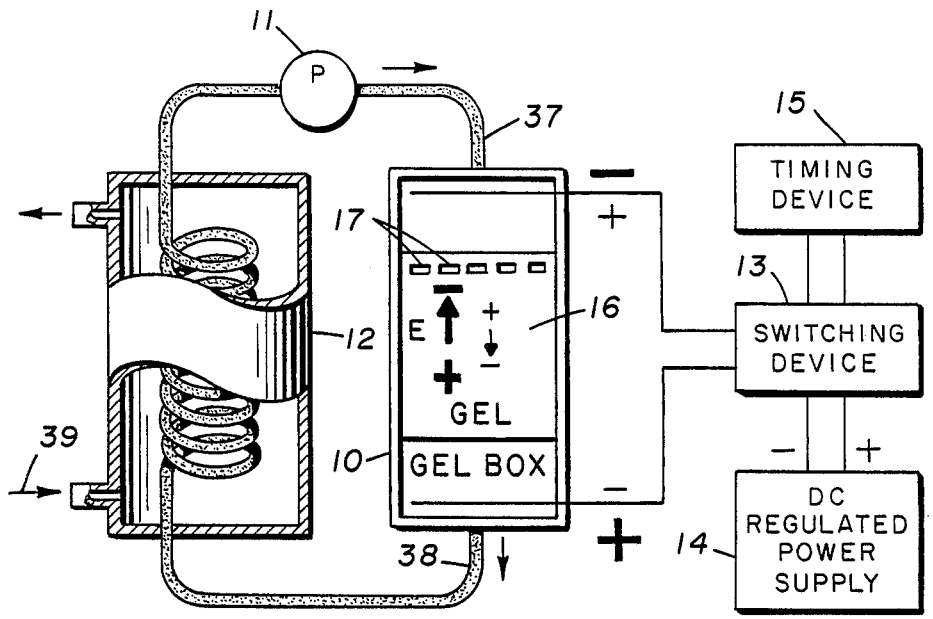
FIG. 1 is a schematic diagram of the field-inversion gel electrophoresis system in one embodiment of the invention.
Figure 2:
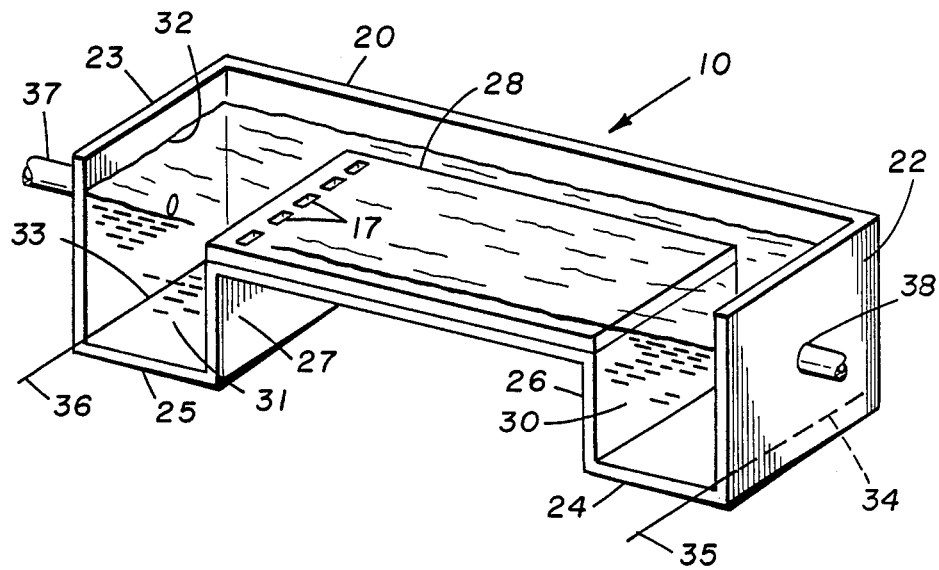
FIG. 2 is a perspective, partly in cut-away view, of a gel box in one embodiment of the invention.
Figure 3:
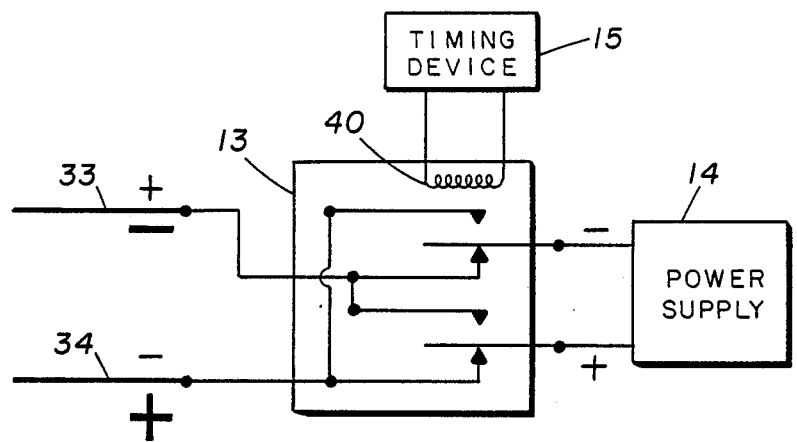
FIG. 3 is a wiring diagram of a switching component to provide switching intervals in the field-inversion gel electrophoresis of FIG. 1.

Referring now to the drawings, a laboratory embodiment of the field-inversion gel electrophoresis system of this invention is illustrated in FIGS. 1 to 3. With particular reference to the schematic diagram in FIG. 1, the field-inversion gel electrophoresis system is illustrated by a series of interconnected components comprising an electrophoresis chamber or gel box 10, a pump 11, a heat exchanger 12, a switching means 13, a DC regulated power supply 14 and a timing device 15.

In the schematic diagram of FIG. 1, a top view of the gel box is illustrated in which the gel layer or slab 16 and a series of sample wells 17 cast into the gel at one end of the gel layer are shown. The longer arrow and larger polarity signs (+ and −) indicate the predominant condition. That is, in variations in which net migration is achieved by applying the same voltage in both directions, the predominant condition is one that is applied for the larger fraction of each switching cycle; in variations in which different voltages are applied for the same interval, the predominant condition would be the higher voltage. The usual convention of arrows pointing from + to − signifying the electrical-field (E) is employed in the figures. Because most macromolecules, including DNA, are negatively charged under electrophoretic conditions, the direction of migration is in the opposite direction of the large arrows.

The internal structure of gel box 10 is shown in greater detail in FIG. 2. The gel box comprises a generally rectangular sided chamber having sidewall 20, endwalls 22 and 23, and base portions 24 and 25. A front sidewall which would lie opposite the rear sidewall 20 is not shown in the cut-away view of FIG. 2. The gel box is further provided with a raised platform or tray 28 in a plane below the top of the gel box and supported at opposite ends by partition walls 26 and 27. This platform serves as a support for the gel layer 16. The side-, end-, and partition-walls at each end of the gel box also form buffer chambers 30 and 31. Buffer is supplied to these buffer chambers in an amount sufficient to cover the gel layer as shown by the buffer level 32.

Electrodes 33 and 34 made of electrochemically inert material and having suitable electrical conducting properties, for example platinum, are provided for retention within the buffer chambers 30 and 31, respectively. They are preferably positioned along the endwalls at the bottom of the buffer chambers with electrical leads 35 and 36 for connection to the switching means 13.

Tubing 37 and 38 with openings into buffer chambers 30 and 31, respectively, are provided for re-circulation of buffer from the gel box through a heat exchanger 12 by pump 11. The heat exchanger serves to dissipate heat generated within the gel box during electrophoresis. The cooling fluid source 39 for the heat exchanger can be provided by a conventional re-circulating, refrigerated water bath (not shown).

The switching means 13 is critical to the provision of the periodic field-inversion of the gel electrophoresis. This system in essence can comprise a power relay device. FIG. 3 is a circuit schematic that indicates the manner in which the power relay can be wired. The relay is shown in its relaxed configuration. When the timing device 15 supplies voltage to the relay's coil 40, the relay switches to its activated configuration, thereby inverting the polarity of the electrodes.

With a switching system as described above, the timing device 15 essentially controls when line voltage is or is not supplied to the coil of the power relay.

The power supply can be any suitable source of direct current.

In the embodiment illustrated by FIGS. 1 to 3, the apparatus is in a configuration that allows field-inversion electrophoresis to be carried out at a constant applied voltage with a larger portion of the switching cycle devoted to forward migration than to reverse migration. In variations in which a higher voltage is applied in one direction than the other, more complex electrical circuitry is required. For example, two power supplies can be employed, wired through separate power relays to independently programmable output circuits of the timing device.

Various components which can be used in the gel electrophoresis apparatus of this invention are commercially available. For example, gel electrophoresis chambers for use in the horizontal mode can be obtained from various sources such as Bethesda Research Laboratories (Gaithersburg, Maryland) Model 144 Horizontal Gel System; Bio-Rad (Richmond, California) Model 1405 and 1415 Electrophoresis Cells; Pharmacia (Uppsala, Sweden) FBE 3000 and GNA-200 Flatbed Cells; and the LKB (Bromma, Sweden) 2117 Multiphore II Electrophoresis Unit. Such devices can be adapted for use in the invention by appropriate combination with the other components specified herein to provide the periodic field-inversion.

Alternatively, the simplified gel box as shown in FIG. 2 can be readily fabricated from rigid plastic material such as, for example, acrylic plastic. Thus, a convenient laboratory scale gel box can be constructed from 0.25 inch thick clear acrylic plastic with inside dimensions 8.5×14 inches as viewed from the top. The gel platform can be 8.5×8.5 inches set in a plane 1.5 inch below the top of the gel box. Buffer chambers at the two ends can extend to a depth of 3.4 inches from the top of the gel box. Electrodes 8.5 inches long, 100% platinum (26 gauge), can be set directly against the intersection of the end walls and the bottom of the buffer chambers.

For a gel box of the foregoing size, buffer can be suitably re-circulated at a rate of about 250 ml/minute using, for example, a Cole Parmer (Chicago, Ill.) Masterflex T-7553-00 drive with a T-7018-21 head equipped with silicone tubing with 5/16 inch inner diameter.

It will be appreciated, however, that the invention is not limited to the foregoing measurements or to the specific illustrative equipment disclosed herein which are provided for exemplification of the invention and not limitation. Other representative equipment which is commercially available can also be used to provide the heat exchanger, switching means, power supply and timing device. Thus the heat exchanger can be fabricated from polyethylene tubing as described by Carle and Olson, *Nucleic Acids Res.* 12, 5647–5664, at 5651 (1984). The cooling fluid source and the ultimate heat sink, can be a Neslab Instruments (Portsmouth, N.H.) Model RTE-9B recirculating, refrigerated water bath.

The power relay can be, for example, a Deltrol Controls (Milwaukee, Wis.), Series 900 DPDT No. 20241-83. For higher voltages or faster switching intervals, various other switching devices are available such as vacuum relays, solid-state relays, and the like.

Illustrative power supplies are the Heathkit (Benton Harbor, Mich.) 18-2717 Regulated High Voltage Power Supply and the Hewlett Packard (Berkeley Hights, N.J.) SCR-1P Model 6448B DC Power Supply.

With a switching system as illustrated above, the timing device merely needs to control when line voltage is or is not supplied to the coil of the power relay. For repetitions of a switching cycle that does not vary during a run, a laboratory timer such as a Lindburg Enterprises (San Diego, Calif.) Chrontrol Model CT-4 can be used. For runs during which the switching cycle is varied, an International Business Machines (Boca Raton, Fla.) Personal Computer can be programmed to produce the desired, temporally varying pattern of standard TTL signals at the output pins of the printer adapter; and these signals can be used to control the line voltage to the coil of the relay in the switching system by way of a Sigma (Braintree, Mass.) Series 226 Model 226R1-5A1 Solid-State Relay.

The following examples will further illustrate the invention although it will be understood that the invention is not limited to these specific examples or the specific details recited therein.

EXAMPLE 1

This example illustrates the separation of DNA's in the size range 15–300 kb using a constant switching cycle in apparatus illustrated by FIGS. 1 to 3. The results are shown in FIG. 4.

Samples included bacteriophage λ DNA cleaved with the restriction endonuclease XhoI, intact bacteriophage λ DNA, DNA from bacteriophage T5 and T4, and total DNA from the yeast (*Saccharomyces cerevisiae*) strain AB972. The λ DNA and the XhoI digest of λDNA were handled by standard sample preparation and gel loading procedures as described by Sealey and Southern, supra. The T4 and T5 DNA's were prepared as described by Carle and Olson, *Nucleic Acids Res.* 12, 5647, 5664 (1984) (hereinafter ref. 1), and the yeast DNA was prepared as described by Carle and Olson, *Proc. Natl. Acad. Sci. USA* 82, 3756–3760 (1985) (hereinafter ref. 2).

The running buffer was 0.5×TBE, as described in Carle and Olson, ref. 1. (1×TBE=90 mM Tris base, 90 mM boric acid, 2.5 mM $Na_2H_2EDTA$, unadjusted pH ~8.2). The switching regime involved 3 sec in the forward direction followed by 1 sec in the backward direction, with this cycle repeated for 12 hr. A constant voltage of 300 V was employed under which conditions the apparatus drew a current of approximately 100 mA. The gel composition was 1% (wt/vol) agarose and the temperature of the recirculating buffer was approximately 13°.

Figure 4:
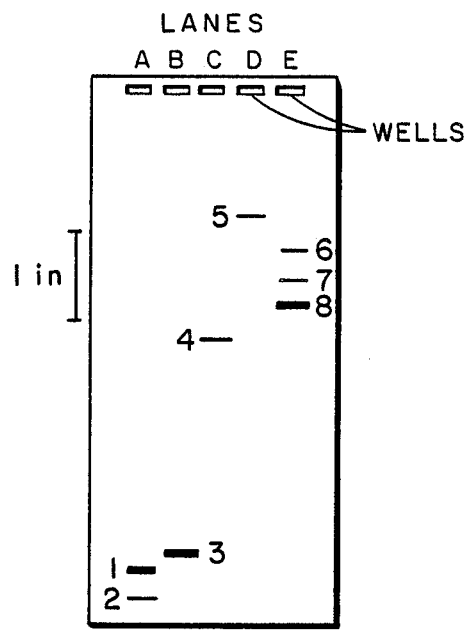
FIG. 4 represents the electrophoretic pattern of bands obtained by field-inversion gel electrophoresis of a series of large molecular weight DNA samples.

FIG. 4 shows the pattern of bands obtained in this example using a 5-lane region of the gel. A scale representing one inch of separation is shown at the left side of FIG. 4. The horizontal lines numbered 1–8 are the bands, which were visualized by conventional ethidium-bromide staining of the gel as described by Sealey and Southern, supra, with the detailed staining and visualization conditions as described by Carle and Olson, refs. 1 and 2. The samples loaded in the 5 lanes were as follows:

A. Bacteriophage λ DNA, cleaved with the restriction enzyme XhoI
   Band 1 (33.5 kb); band 2 (15.0 kb)
B. Bacteriophage λ DNA
   Band 3 (48.5 kb)
C. Bacteriophage T5 DNA
   Band 4 (approx. 125 kb)
D. Bacteriophage T4 DNA
   Band 5 (approx. 170 kb)
E. Yeast (*Saccharomyces cerevisiae*, strain AB972) chromosomal DNA
   Band 6 (chromosome I, est. 260 kb);
   Band 7 (chromosome VI, est. 290 kb);
   Band 8 (approx. 14 remaining chromosomes, est. 300 kb to >1000 kb) As shown in FIG.4, the above conditions provide particularly good separation between λ and T5 DNA. T4 DNA has a lower mobility under these conditions than either the smaller T5 molecule or the larger yeast chromosomes. This phenomenon of a minimum mobility in a particular size range that can be selected by varying the switching regime, is typical of field-inversion gel electrophoresis. The larger yeast chromosomes all have approximately the same mobility under these conditions, producing a single broad band.

EXAMPLE 2

This example illustrates the separation of DNA's in a size range estimated to be 260 kb to >700 kb using a switching-interval gradient with a constant ratio between the forward interval and the backward interval.

The samples were yeast DNA from strains AB972 and A364a, prepared as described in Carle and Olson, ref. 2. The experimental conditions were identical to those in Example 1 with the following exceptions:
  i. The voltage was 260 V.
  ii. The switching regime involved a linearly varying cycle starting at t=0 hr with 9 sec forward, 3 sec backward and ending at t=20 hr (the end of the run) with 60 sec forward and 20 sec backward.

Good separation was obtained of bands 1–9, using the numbering system described in Carle and Olson, ref. 2, and the pattern was qualitatively similar to that obtained by transverse-field gel electrophoresis. For example, the two components of band 5 (bands 5A and 5B, Carle and Olson, ref. 2), were separated in the A364a pattern by approx. 0.3 inch. Three broad, intense bands with lower mobility than band 9 were also present and well separated from one another, but the correspondence of these bands to the bands described in Carle and Olson, ref. 2, was not established. The sizes of the molecules in bands 1–6 have been estimated in Carle and Olson, ref. 1, to span the range 260–700 kb; the molecules in bands 7–9 are thought to be progressively larger than band 6, but size estimates are unavailable.

EXAMPLE 3

This example illustrates the separation of DNA's in a size range estimated to be 260 kb to 700 kb using a linear gradient of forward intervals with a constant backward interval.

The samples and experimental conditions were similar to those in Example 2 with the exception that the switching regime involved a linearly varying forward interval starting at t=0 hr with 10 sec forward and ending at t=12 hr with a forward interval of 60 sec, while the backward interval was held constant at 5 sec. Excellent separation was obtained in the region of bands 1–6, using the numbering system described in Carle and Olson, ref. 2. Once again, the pattern was qualitatively similar to that obtained by transverse-field gel electrophoresis. In comparison to Example 2, better resolution was obtained in the region of bands 1–4, while bands 5 and 6 were more compressed, and the remaining DNA migrated behind band 6 in a broad band with indistinct components. For example, in the AB972 pattern, the overall separation from band 1 to band 4 was approximately 1 inch, with a clear separation of all bands within this interval. The sizes of the molecules in these bands have been estimated in Carle and Olson, ref. 1, to be 260 kb (band 1), 290 kb (band 2), 370 kb (band 3) and 460 kb (band 4).

EXAMPLE 4

This example illustrates the separation of DNA's in the size range 15–300 kb, with particularly effective results in the region from 50–125 kb. Unlike the previous examples, the time interval for the forward and reverse portions of the switching cycle were identical, while the applied voltages differed. The samples were the same as those specified in Example 1. The voltage in the forward direction was 350 V, while that in the reverse direction was 250 V. The switching cycle involved 2 seconds for both the forward and reverse intervals. The overall running time was 16 hours. Other conditions for the test were as described for Example 1. The results were similar to those obtained in Example 1 with the best resolution occurring in the region between λ and T5 DNA. T4 DNA and the smallest yeast chromosome had negligible mobility, while the largest yeast chromosomes all had mobilities similar to that of T5 DNA.

In wiring the apparatus for this test, separate power supplies were employed to apply the forward and reverse voltages. Each power supply was connected to the electrodes through a separate power relay in such a way that the power supply was connected to the electrodes with the appropriate polarity when its relay was activated. The coils of the two relays were connected to independently programmable output circuits of the timing device, which was programmed to incorporate a 0.1 second delay between deactivating one relay and activating the other in order to eliminate the possibility that both relays might be activated simultaneously for a brief interval during the switching event.

Although the inventors are not bound by theory, the phenomenology of the field-invention gel electrophoresis method is believed to be based on the adoption of directional conformations by macromolecules during the electrophoresis, as mentioned above. Presumably, under steady-state electrophoresis, a molecule is to be regarded schematically as an arrow, in which the leading portion of the molecule is in a different conformation than the trailing portion. Also, it is presumed that a molecule has a much higher mobility when the arrow is aligned with the field than when it is mis-aligned, or perhaps even in some intermediate conformation. Furthermore, it is presumed that a size-dependent time interval is required for a molecule to invert the directionality of its conformation. When the field-inversion cycle has a period that is closely matched to the interval required for a molecule's conformational inversion, the molecule is presumed to have very low mobility since it spends little or no time in a conformation that is appropriately aligned with the field. This "resonance" phenomenon explains the minimum-mobility effect described in Example 1, above. Presumably, the largest molecules are completely unable to keep up with the changing fields and adopt a steady-state conformation that has higher mobility than a molecule that is at or near resonance, but still much lower than the mobility of molecules that can re-orient rapidly compared to the field-inversion period. Finally, it should be noted that good temperature control is preferred because it is likely that the activation energy of the conformational changes described above is high enough to impart a temperature dependence to the mobilities of molecules in field-inversion gel electrophoresis that is greater than that observed in conventional electrophoresis.

It is seen from the above that the field-inversion gel electrophoresis can be carried out in a variety of much simpler apparati than required for transverse-field electrophoresis. Indeed, with the exception of the external timing and switching devices and, in some instances improved temperature control, the field-inversion system can be carried out in an ordinary electrophoresis apparatus. This lack of a requirement for a gel box and electrode system of specialized design is of great importance since a large variety of electrophoresis apparati have been designed to maximize the convenience of sample handling and gel preparation, the speed of separations, the amount of sample required, the ease of visualizing the separated molecules, and other experimental variables. In all these cases, it would be useful to be able to separate larger molecules and to increase the resolution in targeted portions of the accessible size range. The field-inversion method offers a general solution to this problem that depends on external accessories rather than the core electrode/running buffer/gel unit. In contrast, as already noted above, transverse-field-alternation gel electrophoresis requires complex electrode geometries, and the precise positioning of the electrodes has dramatic effects on the results obtained. Consequently, transverse-field-alternation gel electrophoresis, unlike the field-inversion technique, does not offer a convenient way of building on and greatly extending the utility of standard electrophoretic practice.

The power of the field-inversion invention lies in the addition of a new variable to a standard electrophoresis run, which profoundly alters the electrophoretic behavior of many types of molecules, while retaining the powerful flexibility that characterizes conventional electrophoresis (i.e. many simple apparatus designs, types of electrophoretic media, etc.). This new variable is the field-inversion switching regime. As indicated in the above examples, the switching regime can be simple (e.g., a constant cycle with 10 sec "forward" and 5 sec "backward") or complex (e.g., a systematically varying cycle during a run), depending on the desired result. A dramatic illustration of the power of the switching regime to alter electrophoretic mobilities is provided by the minimum-mobility phenomenon: under some conditions a strong direct (rather than the usual inverse) correlation between size and mobility can be created. This "limb" of the size-mobility curve may be more effective than the conventional limb for some separations. When it is undesirable, because it leads to a region in the gel in which molecules of two greatly different sizes can unexpectedly have the same mobility, it can be minimized or eliminated by the use of switching-interval gradients, or appropriately chosen constant switching cycles.

As is the case with conventional electrophoresis, in field-inversion gel electrophoresis, large numbers of samples that have been loaded onto adjacent lanes of a single gel will migrate in parallel with one another, experiencing closely comparable electrophoretic conditions. The ability to make reliable, lane-to-lane comparisons between many samples on the same gel is one of the strongest features of conventional electrophoresis. It may or may not be possible to achieve simple, parallel migration patterns by the transverse-field technique, but most reported applications have failed to achieve this goal. The importance of this point arises because many electrophoretic procedures depend on comparisons between the mobilities of molecules migrating in different lanes, and experimental flexibility is at a maximum when good comparisons can be made between samples that are several lanes apart. One example of an application of this type is the estimation of molecular sizes by comparing the mobility of a molecule of unknown size in one lane with that of a molecule of known size in a different lane. Another example, which does not require absolute size calibration, concerns efforts to determine whether or not molecules in different samples are potentially identical or demonstrably non-identical by determining whether or not they have the same or different mobilities.

Because of its capability of enhancing standard electrophoretic practice while imposing minimal demands on the design of the core components of an electrophoresis apparatus or the distribution of samples across a gel, field-inversion electrophoresis has a wide spectrum of potential applications. Its capability of enhancing the ability to resolve large DNA molecules has been demonstrated above over a size range from 15 kb to >700 kb, where the uncertainty in the upper limit of the demonstrated range of application arises because of a lack of well characterized test molecules >700 kb in size. It is highly likely that the applicable size range can be expanded both to smaller and larger sizes by changes in such easily varied test conditions as the temperature, the switching regime, the composition of the electrophoretic medium, the forward and/or backward voltage, the composition of the running buffer, and the duration of the run. All these variables can be optimized for the best results for specific applications of the electrophoresis in which more sensitive effects could be obtained with the field-inversion method than with conventional electrophoresis.

Similarly, the applications of the field-inversion technique are not limited to DNA. The qualitative electrophoretic behavior of other charged macromolecules such as RNA, protein, nucleoprotein particles, and protein-detergent complexes is generally similar to that of DNA, and the field-inversion method is expected to increase the size range over which these molecules can be separated and allow enhanced resolution in particular size ranges that are targeted by an appropriate choice of the switching regime.

Various other examples of the invention will be apparent to the person skilled in the art after reading the disclosure herein and it is intended that all such examples be included in the scope of the appended claims.

We claim:

1. An electrophoresis method to effect differential net migration, the extent of said migration being dependent on molecular size, of electrically charged macromolecular substances through a gel support in a single dimension, which method comprises:

subjecting electrically charged macromolecular substances selected from the group consisting of DNA, RNA, and detergent-protein complexes applied to a gel support to the repeated inversion of an electrical field along a single dimension, wherein the repeated inversion comprises cycles each consisting essentially of a first voltage in one direction of polarity for a first time interval, and a second voltage in the opposite direction of polarity for a second time interval, wherein the migration effected by the total first voltages and first time intervals over all cycles does not equal the migration effected by the second voltages and second time intervals over all cycles, thus resulting in a net differential migration of said substances.

2. The method of claim 1 wherein each first voltage is equal to each second voltage and the total of the first time intervals is different from the total of the second time intervals.

3. The method of claim 1 wherein each first time interval is equal to each second time interval and each first voltage is different from each second voltage.

4. The method of claim 1 wherein for each successive cycle the first voltage bears the same ratio to the second voltage and the first time interval is equal to the second time interval, and wherein the magnitudes of said first and second voltages are monitonically greater or less in each successive cycle.

5. The method of claim 1 wherein for each successive cycle, the first time interval bears the same ratio to the second time interval, and the first voltage is equal to the second voltage, and wherein the first and second time intervals are monitonically greater or less in each successive cycle.

6. The method of claim 1 wherein the electrophoresis gel support is an agarose gel.

7. The method of claim 1 wherein the substances are DNA molecules of about 15 kb or greater.

8. The method of claim 1 wherein the substances are applied at the same position in the gel support with respect to said single dimension.

9. The method of claim 8 wherein the substances form a mixture and said method results in a separation of the substances.

10. The method of claim 8 wherein the substances are applied next to each other at said position so as to migrate in parallel lines in the gel.

11. In a gel electrophoresis method to effect differential net migration of electrically charged marcomolecular substances through a gel support in a single dimension, wherein the net migration for each of said substances is a function of the size of said substance, the improvement which comprises subjecting substances selected from the group consisting of DNA, RNA, and detergent-protein complexes, which have been applied to an electrophoresis gel support, to the repeated inversion of an electrical field along a single dimension, wherein the repeated inversion comprises cycles each consisting essentially of a first voltage in one direction of polarity for a first time interval and a second voltage in the opposite direction of polarity for a second time interval.

12. The method of claim 11 wherein each first voltage is equal to each second voltage and the total of the first time intervals is different from the total of the second time intervals.

13. The method of claim 11 wherein wherein each first time interval is equal to each second time interval and each first voltage is different from each second voltage.

14. The method of claim 11 wherein for each successive cycle the first voltage bears the same ratio to the second voltage and the first time interval is equal to the second time interval, and wherein the magnitudes of said first and second voltages are monitonically greater or less in each successive cycle.

15. The method of claim 11 wherein for each successive cycle, the first time interval bears the same ratio to the second time interval, and the first voltage is equal to the second voltage, and wherein the first and second time intervals are monitonically greater or less in each successive cycle.

16. The method of claim 11 wherein the electrophoresis gel support is an agarose gel.

17. The method of claim 11 wherein the substances are DNA molecules of about 15 kb or greater.

18. The method of claim 11 wherein the substances are applied at the same position in the gel support with respect to said single dimension.

19. The method of claim 18 wherein the substances form a mixture and said method results in a separation of the substances.

20. The method of claim 18 wherein the substances are applied next to each other at said position so as to migrate in parallel lines in the gel.

* * * * *